United States Patent
Beaussant Törne et al.

(10) Patent No.: US 12,239,673 B2
(45) Date of Patent: Mar. 4, 2025

(54) COMPOSITION COMPRISING PEDIOCOCCUS PENTOSACEUS FOR USE IN TREATMENT AND/OR PREVENTION OF FOOD AND/OR ALCOHOL POISONING

(71) Applicant: Evaggelos Schjölin, Tyresö (SE)

(72) Inventors: Eric Beaussant Törne, Tyresö (SE); Evaggelos Schjölin, Tyresö (SE)

( * ) Notice: Subject to any disclaimer, the term of this patent is extended or adjusted under 35 U.S.C. 154(b) by 0 days.

(21) Appl. No.: 18/555,515

(22) PCT Filed: Aug. 11, 2022

(86) PCT No.: PCT/EP2022/072523
§ 371 (c)(1),
(2) Date: Oct. 14, 2023

(87) PCT Pub. No.: WO2023/030850
PCT Pub. Date: Mar. 9, 2023

(65) Prior Publication Data
US 2024/0189370 A1     Jun. 13, 2024

(30) Foreign Application Priority Data

| | | |
|---|---|---|
| Aug. 31, 2021 | (SE) | 2151087-0 |
| Dec. 7, 2021 | (SE) | 2151493-0 |
| Dec. 8, 2021 | (SE) | 2151496-3 |

(51) Int. Cl.
*A61K 35/744* (2015.01)
*A61K 36/064* (2006.01)
*A61P 25/32* (2006.01)

(52) U.S. Cl.
CPC .......... *A61K 35/744* (2013.01); *A61K 36/064* (2013.01); *A61P 25/32* (2018.01)

(58) Field of Classification Search
CPC combination set(s) only.
See application file for complete search history.

(56) References Cited

U.S. PATENT DOCUMENTS

| | | |
|---|---|---|
| 9,579,353 B2 | 2/2017 | Olmstead |
| 2006/0263385 A1 | 11/2006 | Gare |
| 2012/0315249 A1* | 12/2012 | Olmstead ............. A61K 35/744 424/93.3 |
| 2014/0335187 A1* | 11/2014 | Carpenter ................ A61K 9/20 424/93.3 |
| 2016/0354417 A1 | 12/2016 | Smittle et al. |
| 2018/0333441 A1 | 11/2018 | Chung |

FOREIGN PATENT DOCUMENTS

| | | |
|---|---|---|
| CN | 103764154 A | 4/2014 |
| CN | 112189760 A | 1/2021 |
| EP | 3415155 A1 | 12/2018 |
| JP | 2015525780 A | 9/2016 |
| KR | 101109746 B1 | 5/2011 |
| WO | 2011044516 A2 | 4/2011 |
| WO | 2014022279 A2 | 2/2014 |

OTHER PUBLICATIONS

Rondanelli, Mariangela, et al. "Effects of 60-day *Saccharomyces boulardii* and superoxide dismutase supplementation on body composition, hunger sensation, pro/antioxidant ratio, inflammation and hormonal lipo-metabolic biomarkers in obese adults: a double-blind, placebo-controlled trial." (Year: 2021).*
HH-PP57 (retrieved from https://www.alibaba.com/product-detail/HACCP-FSSC22000-Certified-Long-shelf-life_1600983882527.html on Aug. 6, 2024). (Year: 2020).*
Katkuri, Mounika. "A Review on Liver Exploring upon Toxic Substances like Alcohol Poisoning." Sep. 2016 (Year: 2016).*
Kang, Y. James, and Zhanxiang Zhou. "Zinc prevention and treatment of alcoholic liver disease." Molecular aspects of medicine 26.4-5 (2005): 391-404. (Year: 2005).*
Gastritis and Food poisoning (The Hidden Causes of Acute Gastritis You Need to Know By: GI Alliance Jul. 26, 2019, retrieved from https://gialliance.com/gastroenterology-blog/the-hidden-causes-of-acute-gastritis-you-need-to-know#:~:text=Food%20poisoning.,that%20come%20with%20acute%20gastritis. (Year: 2019).*
Office action CN patent office of 202210025296.7 dated Apr. 4, 2024 (and CN to EN machine translation).
Jiang S. et al., "Pediococcus pentosaceus, a future additive or probiotic candidate" (2021) (cited in SE patent office dated Mar. 16, 2022).
Office action SE patent office of SE2151087-0 dated Mar. 16, 2022 (parent case).
Int'l Search Report and Written Opinion in Parent WIPO case, Nov. 24, 2022.
Written Opinion of the International Preliminary Examining Authority in Parent WIPO Case (WO/IPEA), Aug. 30, 2023 (the PPH request is based on this document).
Written Opinion of the International Preliminary Examining Authority in Parent WIPO Case (WO/IPEA), Feb. 9, 2023.
Applicant Response dated Feb. 15, 2023 to WO of IPEA dated Feb. 9, 2023, including claim amendments. PPH request is based on the Aug. 30, 2023 WO of IPEA which considered these claims.

(Continued)

*Primary Examiner* — Robert J Yamasaki
*Assistant Examiner* — Trevor Kane
(74) *Attorney, Agent, or Firm* — Welsh IP Law LLC (57) ABSTRACT

The present invention relates to a composition comprising *Pediococcus pentosaceus*, one or more yeast, wherein a weight ratio of *Pediococcus pentosaceus*:yeast is between 0.01 to 0.5:1, and optionally one or more minerals, sugar and pharmaceutical acceptable excipients, additives and/or adjuvants. The invention also relates to a use of the composition as food supplement or in treatment and/or prevention of a disease in a mammal, such as a human and a use in treatment and/or prevention of food and/or alcohol poisoning in a mammal.

16 Claims, 1 Drawing Sheet

(56) References Cited

OTHER PUBLICATIONS

Office action EP patent office of 22765443.1 dated Mar. 14, 2024.
English Translation of Office action CN patent office of 202210025296.7 dated Oct. 13, 2023 in related case.
Wang Xiaonan et al., https://zhuanlan.zhihu.com/p/361416799?utm_id=0 , pp. 1 7, (Includes English translation).
"Extraction of and Research on Cytoso lic Aldehyde Dehydrogenase from *Saccharomyces cerevisiae* , Zhou Bai ling et al, Liquor Making Science & Technology, Tol. 180, p. 28 30" (includes English translation).

\* cited by examiner

COMPOSITION COMPRISING PEDIOCOCCUS PENTOSACEUS FOR USE IN TREATMENT AND/OR PREVENTION OF FOOD AND/OR ALCOHOL POISONING

FIELD OF THE INVENTION

The present invention relates to a composition comprising *Pediococcus pentosaceus*, one or more yeast, wherein a weight ratio of *Pediococcus pentosaceus*:yeast is between 0.01 to 0.5:1, and optionally one or more minerals, sugar and pharmaceutical acceptable excipients, additives and/or adjuvants. The invention also relates to a use of the composition in treatment and/or prevention of a disease in a mammal, such as a human and a use in treatment and/or prevention of food and/or alcohol poisoning in a mammal. The invention also relates to a use of the composition as a food supplement.

BACKGROUND OF THE INVENTION AND PRIOR ART

Food or alcohol poisoning deplete the mammal body of fluids, salts, vitamins and energy. During and after food or alcohol poisoning, the mammal body is in need for fluid, salt, mineral, vitamins and energy replacement. The illness caused by bacteria/virus/fungi must be removed from the mammal body, i.e. the body must recover after the illness Most antibiotics affect normal fluid and salt balance in the body. Also, alcohol affects fluid and salt balance. Furthermore, food and alcohol poisoning negatively affect microbiotic flora in the intestines. This flora must be restored/repaired after removal of the bacteria/virus/fungi and alcohol, which repair is energy consuming for the body.

Products used during food and alcohol poisoning are fluid replacement products used to supply the body with fluids and salts. Some of the products may include vitamins, such as vitamin B and C. These same products may be used after a training session to prevent or overcome muscle aches.

The bacteria *Pediococcus pentosaceus* (*P. pentosaceus*) is a gram-positive, homo-fermentative, facultative anaerobic lactic acid bacteria. *Pediococcus pentosaceus* is used in fermentation processes, e.g. for the production of Mediterranean traditional sausages. *Pediococcus pentosaceus* has gained interest in both the food and medical field because of its positive effects as a probiotic. *Pediococcus pentosaceus* has been tested against *Salmonella* and *Streptococcus* and *E. coli*, as well as for treatment of alcohol induced liver injuries, such as alcohol liver disease. *Pediococcus pentosaceus* is general recognized as safe (GRAS) by the FDA.

Yeast, especially nutritional yeast, is rich in nutrients, salts and vitamins. Yeast may even be fortified with more vitamins. Yeast may be used as a probiotic.

*Saccharomyces cerevisiae* is the main source of nutritional yeast, which is sold commercially as a food product. It is popular with vegans and vegetarians as an ingredient in cheese substitutes, or as a general food additive as a source of vitamins and minerals, especially amino acids and B-complex vitamins.

Several clinical and experimental studies have shown that *Saccharomyces cerevisiae* var. *boulardii* is, to lesser or greater extent, useful for prevention or treatment of several gastrointestinal diseases. *Saccharomyces cerevisiae* var. *boulardii* seems to reduce risk for antibiotic-associated diarrhea both in adults and in children and to reduce risk of adverse effects of *Helicobacter pylori* eradication therapy. Also, some limited evidence supports efficacy of *Saccharomyces cerevisiae* var. *boulardii* Hansen CBS 5926 in prevention (but not treatment) of Hansen CBS 5926 diarrhea and, at least as an adjunct medication, in treatment of acute diarrhea in adults and children and of persistent diarrhea in children. It may also reduce symptoms of allergic rhinitis. Administration of *S. cerevisiae* var. *boulardii* is considered generally safe. In clinical trials, it was well tolerated by patients, and adverse effects rate was similar to that in control groups (i.e. groups with placebo or no treatment). No case of *S. cerevisiae* var. *boulardii* fungemia has been reported during clinical trials.

Defeating food and alcohol poisoning today is still a slow process, which may take several days or weeks. There are no products on the market to provide the body with all nutrients and minerals etc. needed to bring back the balance in the body after poisoning. There is a need for products that help recovery after poisoning and improve the time needed to recover. There is a need for reducing socioeconomical problems related to hangovers. There is a need for a product that increases the rate by which alcohol and its metabolic products can be removed from the human body.

US20106263385 describes a product that can be used to counter the side effects of alcohol intake, "hangover". The product includes bacteria (not *Pediococcus pentosaceus*) (11-12 wt %), yeast (0.1 wt %), sugar (22-25 wt %), minerals and among others milk thistle, N-acetyl-L-cysteine and vitamins B and C. No results are shown of the effect of this complex and expensive product. The product tablet is large and has a weight of 4000 to 5000 mg. Such large tablets are difficult to administer.

US2014335187 describes a product that counteracts the toxic effects of alcohol. The product contains a mixture of anaerobically fermented bacteria (*Pediococcus pentosaceus, Pediococcus acidilactici* and *Lactobacillus plantarum*) in an amount of 58 wt % and sugar, vitamins and minerals and other ingredients. The results show an effect that is slightly better than the effect of a comparison product that does not include bacteria.

KR101109746 describes a new *Pediococcus pentosaceus* strain that can be used against food poisoning.

Jiang et al, Microb Cell Fact 2021, 20:45, p 1-14, publ. 16 Feb. 2021, shows that *Pediococcus pentosaceus* can be used in food poisoning and detoxification or as a food supplement.

Some products that reduce alcohol poisoning, for example as developed by Prof. Yungfeng Lu, University of California, contain enzymes. These products have been tested in mice. Even if successful in humans, such products are expensive to manufacture.

SUMMARY OF THE INVENTION

It is an object of the present invention to at least partly overcome the above-mentioned problems, and to provide an improved composition for use in food or alcohol poisoning or for improved recovery from food or alcohol poisoning.

This object is achieved by a composition comprising or consisting of *Pediococcus pentosaceus*.

This object is achieved by a composition comprising or consisting of *Pediococcus pentosaceus*, one or more yeast, wherein a weight ratio of *Pediococcus pentosaceus*:yeast is between 0.01 to 0.5:1, and optionally one or more minerals, sugar and pharmaceutical acceptable excipients, additives and/or adjuvants. In some aspects, the composition comprises or consists of *Pediococcus pentosaceus* in an amount of 5 or 10 wt % or less at $10^3$ to $10^{15}$ CFU/g, and one or more yeast in an amount of 50 wt % or less at $10^5$ to $10^{15}$ CFU/g, wherein weight percentages are percentages of the total composition.

In some aspects, the composition comprises or consists of *Pediococcus pentosaceus* in an amount of 5 wt % or less at $10^3$ to $10^{15}$ CFU/g and one or more yeast in an amount of 25 wt % or less at $10^5$ to $10^{15}$ CFU/g, wherein a weight ratio of *Pediococcus pentosaceus*:yeast is between 0.01 to 0.5:1, wherein weight percentages are percentages of the total composition, and optionally one or more minerals, sugar and pharmaceutical acceptable excipients, additives and/or adjuvants.

In some aspects, *P. pentosaceus* is present in an amount of 5 wt % or less at $10^5$ to $10^8$ CFU/g.

In some aspects, *P. pentosaceus* is present in an amount of 1 wt % or less at $10^3$ to $10^{15}$ CFU/g.

In some aspects, *P. pentosaceus* is present in an amount of 1 wt % or less at $10^5$ to $10^8$ CFU/g.

In some aspects, *Pediococcus pentosaceus* is *P. pentosaceus* strain HH-PP57.

In some aspects, the one or more yeast is *Saccharomyces cerevisiae* var. *boulardii*, such as strain CNCM I-1079 or strain DBVPG6763.

In some aspects, *Pediococcus pentosaceus* is the sole bacterium used in the composition. In some aspects, *Pediococcus pentosaceus* is not fermented. In some aspects, *Pediococcus pentosaceus* is not anaerobic fermented.

The unique combination of ingredients in the composition of the invention provides for an improved recovery from food or alcohol poisoning. The *Pediococcus pentosaceus* works as a probiotic agent. It is believed to inhibit growth of pathogenic bacteria and may thus be used for detoxing the body of a mammal from toxic bacteria/fungi/viruses, as well as having an anti-inflammatory and antioxidant function. It is also believed to improve motility of the intestines. It is further believed to improve uptake of salts and minerals in the intestine.

*Pediococcus pentosaceus* is believed to breakdown alcohols and aldehydes. Especially after alcohol poisoning, ethanol and its metabolic products, such as ethanal and aldehydes, must be removed to overcome the poisoning. *Pediococcus pentosaceus* improves the breakdown/removal of alcohols and its metabolic products and thus improves the recovery of an alcohol poisoning.

The prior art suggests doses for probiotics that are billions times higher compared to the dose used in the composition of the invention. The minor effects disclosed in the prior art seem to be a result of a combination of specific probiotics at extreme high doses. The risk for side effects may increase when using such high doses. The intestine mobility for example is increased by *P. pentosaceus*. At high dose, the increase in mobility of the intestine may cause side effects. By using a much (billion times) lower dose, the side effects can be prevented.

There are neither any data available for a composition comprising only one probiotic, such as *P. pentosaceus*. The known literature seems to teach away from the use of *P. pentosaceus* as the sole bacterium/probiotic.

However, excellent results have been obtained using *P. pentosaceus* as a sole bacterium at a low dose of 5 or 10 wt % or less at $10^3$ to $10^{15}$ CFU/g, or even 1 wt % or less at $10^5$ to $10^9$ CFU/g. The fact that only one bacterium can be used and the fact that this bacterium can be used at a low dose, reduces possible side effects and costs for production and manufacturing of the composition. This is especially interesting at large scale production.

Yeast includes minerals, fatty acids and vitamins, all of which are needed to overcome or recover from food or alcohol poisoning. Yeast may be fortified with vitamins.

Both *P. pentosaceus* and yeast have been suggested for treatment of several diseases. Like, *P. pentosaceus* (in combination with other probiotics/bacterium), yeast has also been tested at doses that are billion times higher compared to the doses present in the composition of the invention. High doses may lead to unwanted side effects. In contrast to the known literature, it was found that excellent results can be obtained when yeast is used at a low dose of 50 wt % or less at $10^5$ to $10^{15}$ CFU/g, or even 10 wt % or less at $10^6$ to $10^{12}$ CFU/g, in combination with low doses of *P. pentosaceus* as mentioned above. The fact that only one bacterium can be used and the fact that the bacterium and the yeast can be used at a low dose, reduces possible side effects and costs for production and manufacturing of the composition. This is especially interesting at large scale production.

The weight ratio of *Pediococcus pentosaceus*:yeast is between 0.01 to 0.5:1. In some aspects, the weight ratio is between 0.01 to 0.1:1, or 0.03 to 0.08:1. The unique ratio allows use of both *P. pentosaceus* and yeast at low amounts in the composition of the invention. It is believed that there is a synergistical effect when using *P. pentosaceus* and the yeast at these ratios.

A synergistical effect seems to exist between *P. pentosaceus* and the one or more yeast for removal of harmful substances and bacteria from the body. Together, they seem to be useful for prevention and/or treatment of food poisoning or alcohol poisoning. Together they are believed to be useful for the prevention and/or treatment of diseases, such as gastrointestinal diseases, diarrhea, especially acute diarrhea. Together they are believed to be useful for restoring fluids, salts, vitamins and energy in the mammal body during and/or after a food or alcohol poisoning.

The object is also achieved by a composition comprising or consisting of *Pediococcus pentosaceus*, one or more yeast, one or more minerals, and optionally sugar, pharmaceutical acceptable excipients, additives and/or adjuvants.

In some aspects, the minerals are selected from the group comprising or consisting of zinc, magnesium, sodium and calcium. In some aspects, the minerals are selected from the group comprising or consisting of zinc sulfate, magnesium oxide, sodium chloride and calcium carbonate.

In some aspects, the composition comprises or consists of *Pediococcus pentosaceus* in an amount of 10 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, and zinc salt or zinc sulfate in an amount of 0.01 to 5 wt %, wherein weight percentages are percentages of the total composition, and optionally one or more minerals, sugar and pharmaceutical acceptable excipients, additives and/or adjuvants.

Zinc is used in food supplements, in oral rehydration therapy (ORT) and as an astringent (a chemical that shrinks or constricts body tissues). During and after food and/or alcohol poisoning, the body becomes dehydrated. The presence of zinc in the composition improves rehydration of the body and may thereby be useful in prevention and recovery/treatment of food and/or alcohol poisoning or another disease, such as gastrointestinal diseases, diarrhea, especially acute diarrhea. The amount of zinc salt or zinc sulfate is preferably kept below 5 or 2 wt % to prevent side effects that may be caused by zinc overdosing.

Zinc is also used in the brewing process for optimal yeast health and performance. Without wanting to be bound by any theories, the presence of zinc may improve the performance of the one or more yeast and possibly the probiotic *P. pentosaceus*. This may explain why both *P. pentosaceus* and yeast are effective at doses that are billion times lower than known effective doses of both yeast and *P. pentosaceus*.

A combination of zinc and probiotic is believed to be more effective in the treatment of Antibiotic-associated Diarrhea as opposed to when probiotic was given alone.

Zinc seems to promote the repair of the intestinal mucosa. When a combination of zinc and probiotic is used, there is believed to be an advanced decrease in plasma diamine oxidase (DAO) activity, which is released following damage to the epithelial cells of the intestinal mucosa.

Zinc also deals with the restoration of the mucosal barrier integrity and enterocyte brush-border enzyme activity. Moreover, zinc promotes the function of the immune system and enhances mucosal repair.

In some aspects, the composition comprises or consists of *Pediococcus pentosaceus* in an amount of 10 wt % or less at 10 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, and magnesium salt or magnesium oxide in an amount of 0.01 to 20 wt %, wherein weight percentages are percentages of the total composition, and optionally one or more minerals, sugar and pharmaceutical acceptable excipients, additives and/or adjuvants.

Magnesium is used in food supplements, for relief of heartburn and dyspepsia, as an antacid (a substance that neutralizes stomach acidity) and is used to relieve heartburn, indigestion or an upset stomach), and as a short-term laxative. Magnesium may be used in the treatment of constipation and diarrhea. During and after food and/or alcohol poisoning, the stomach may be upset, i.e. the production of acid in the stomach may be increase due to a disease or poisoning. The presence of magnesium in the composition reduces the acidity of the stomach fluid and may thereby be useful in prevention and recovery/treatment of food and/or alcohol poisoning or another disease, such as gastrointestinal diseases, diarrhea, especially acute diarrhea. The amount of magnesium salt or magnesium oxide is preferably kept below 20 or 10 wt % to prevent side effects that may be caused by magnesium overdosing.

Without wanting to be bound by any theories, the presence of magnesium may improve the performance of the yeast and possibly the probiotic *P. pentosaceus*. A reduced acidity of the stomach fluid may improve the effectivity of *P. pentosaceus* and/or yeast. This may explain why both *P. pentosaceus* and yeast are effective at doses that are billion times lower than known effective doses of both yeast and *P. pentosaceus*.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, zinc salt or zinc sulfate in an amount of 0.01 to 5 wt % and magnesium salt or magnesium oxide in an amount of 0.01 to 20 wt %, wherein weight percentages are percentages of the total composition, and optionally sugar, pharmaceutical acceptable excipients, additives and/or adjuvants.

As mentioned above, both zinc and magnesium or salts thereof, are used in food supplements and both may be useful in prevention and recovery/treatment of food and/or alcohol poisoning or another disease, such as gastrointestinal diseases, diarrhea, especially acute diarrhea. Both zinc and magnesium may have a synergistic effect on *P. pentosaceus* and yeast. Possibly, by lowering the acidity in the stomach fluid by magnesium and additionally rehydrating the body and stimulating the efficiency of the yeast (and possibly *P. pentosaceus*) by zinc, the overall efficiency and effectiveness of the composition in preventing and treating the mentioned diseases/poisonings of the human body is improved.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, and calcium salt or calcium carbonate in an amount of 0.01 to 50 wt %, wherein weight percentages are percentages of the total composition, and optionally sugar, pharmaceutical acceptable excipients, additives and/or adjuvants.

Calcium or calcium carbonate is used in food supplements. Calcium is also used as an antacid. Like magnesium, calcium lowers the acidity of the stomach fluid. Calcium is further used as a phosphate binder for the treatment of hyperphosphatemia and for maintenance of haemodialysis and prevention and treatment of osteoporosis. During and after food and/or alcohol poisoning, the stomach may be upset, i.e. the production of acid in the stomach may be increase due to a disease or poisoning. The presence of calcium in the composition reduces the acidity of the stomach fluid and may thereby be useful in prevention and recovery/treatment of food and/or alcohol poisoning or another disease, such as gastrointestinal diseases, diarrhea, especially acute diarrhea. Calcium has been shown to have a beneficial influence on the microbiota in the gut. This is a result of the formation of amorphous calcium phosphate, which binds bile acids and other cytotoxic substances in the gut. Due to the precipitation of cytotoxic substances, the environment of the gut becomes less aggressive and possibly also influences the adhesion of the microbiota. The amount of calcium salt or calcium carbonate is preferably kept below 50 or 20 wt % to prevent side effects that may be caused by calcium overdosing.

Without wanting to be bound by any theories, the presence of calcium may improve the performance of the yeast and possibly the probiotic *P. pentosaceus*. A reduced acidity of the stomach fluid may improve the effectivity of *P. pentosaceus* and/or yeast in the stomach. This may explain why both *P. pentosaceus* and yeast are effective at doses that are billion times lower than known effective doses of both yeast and *P. pentosaceus*.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, zinc salt or zinc sulfate in an amount of 0.01 to 5 wt % and calcium salt or calcium carbonate in an amount of 0.01 to 50 wt %, wherein weight percentages are percentages of the total composition, and optionally sugar, and pharmaceutical acceptable excipients, additives and/or adjuvants.

As mentioned above, both zinc and calcium or salts thereof, are used in food supplements and both may be useful in prevention and recovery/treatment of food and/or alcohol poisoning or another disease, such as gastrointestinal diseases, diarrhea, especially acute diarrhea. Both zinc and calcium may have a synergistic effect on *P. pentosaceus* and yeast. Possibly, by lowering the acidity in the stomach fluid by calcium and additionally rehydrating the body and stimulating the efficiency of the yeast (and possibly *P. pentosaceus*) by zinc, the overall efficiency and effectiveness of the composition in preventing and treating the mentioned diseases/poisonings of the human body is improved.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, zinc salt or zinc sulfate in an amount of 0.01 to 5 wt %, magnesium salt or magnesium oxide in an amount of 0.01 to 20 wt % and calcium salt or calcium carbonate in an amount of 0.01 to 50 wt %, wherein weight percentages are percentages of the total composition, and optionally sugar, and pharmaceutical acceptable excipients, additives and/or adjuvants.

As mentioned above, zinc, magnesium and calcium or salts thereof, are used in food supplements and may be useful in prevention and recovery/treatment of food and/or alcohol poisoning or another disease, such as gastrointestinal diseases, diarrhea, especially acute diarrhea. Zinc, magnesium and calcium may have a synergistic effect on *P. pentosaceus* and yeast. Possibly, by lowering the acidity in the stomach fluid by magnesium and calcium, and additionally rehydrating the body and stimulating the efficiency of the yeast (and possibly *P. pentosaceus*) by zinc, the overall efficiency and effectiveness of the composition in preventing and treating the mentioned diseases/poisonings of the human body is improved.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, and sodium salt or sodium chloride in an amount of 0.01 to 90 wt %, wherein weight percentages are percentages of the total composition, and optionally sugar, and pharmaceutical acceptable excipients, additives and/or adjuvants.

Sodium is an electrolyte that regulates the amount of water in your body. Sodium also plays a part in nerve impulses and muscle contractions. Sodium chloride is used to treat or prevent sodium loss caused by dehydration, excessive sweating, or other causes. During and after food and/or alcohol poisoning or due to a disease, the amounts of electrolytes in the body are decreased and often need to be replenished. The presence of sodium in the composition may therefore be useful in prevention and recovery/treatment of food and/or alcohol poisoning or another disease, such as gastrointestinal diseases, diarrhea, especially acute diarrhea. The presence of sodium in the composition may therefore be useful in prevention and recovery/treatment of muscle aches.

Sodium may have a synergistic effect on *P. pentosaceus* and yeast. Possibly, by rehydrating the body, the overall efficiency and effectiveness of the composition in preventing and treating the mentioned diseases/poisonings of the human body is improved.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, zinc salt or zinc sulfate in an amount of 0.01 to 5 wt %, and sodium salt or sodium chloride in an amount of 0.01 to 90 wt %, wherein weight percentages are percentages of the total composition, and optionally sugar, and pharmaceutical acceptable excipients, additives and/or adjuvants.

As mentioned above, both zinc, sodium or salts thereof, are used in food supplements and both may be useful in prevention and recovery/treatment of food and/or alcohol poisoning or another disease, such as gastrointestinal diseases, diarrhea, especially acute diarrhea. Zinc, and sodium may have a synergistic effect on *P. pentosaceus* and yeast. Possibly, by rehydrating the body by zinc and sodium and additionally stimulating the efficiency of the yeast (and possibly *P. pentosaceus*) by zinc, the overall efficiency and effectiveness of the composition in preventing and treating the mentioned diseases/poisonings of the human body is improved.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, zinc salt or zinc sulfate in an amount of 0.01 to 5 wt %, sodium salt or sodium chloride in an amount of 0.01 to 90 wt %, and magnesium salt or magnesium oxide in an amount of 0.01 to 20 wt % and/or calcium salt or calcium carbonate in an amount of 0.01 to 50 wt %, wherein weight percentages are percentages of the total composition, and optionally sugar, and pharmaceutical acceptable excipients, additives 5 and/or adjuvants.

As mentioned above, zinc, sodium, magnesium and calcium or salts thereof, are used in food supplements and may be useful in prevention and recovery/treatment of food and/or alcohol poisoning or another disease, such as gastrointestinal diseases, diarrhea, especially acute diarrhea. Zinc, sodium, magnesium and calcium, alone or in any combination, may have a synergistic effect on *P. pentosaceus* and yeast. Possibly, by lowering the acidity in the stomach fluid by magnesium and/or calcium, and additionally rehydrating the body by zinc and sodium and stimulating the efficiency of the yeast (and possibly *P. pentosaceus*) by zinc, the overall efficiency and effectiveness of the composition in preventing and treating the mentioned diseases/poisonings of the human body is improved.

This object is also achieved by a composition comprising or consisting of *Pediococcus Pentosaceus*, one or more yeast, one or more minerals, sugar and pharmaceutical acceptable excipients, additives and/or adjuvants.

In some aspects, the sugar is selected from the group comprising or consisting of fructose, sucrose, dextrose, acesulfame K, alitame, aspartame, dextrose, fructose, galactose, inulin, isomalt, lactitol, maltitol, maltose, mannitol, neohesperidin dihydrochalcone, saccharin, sodium cyclamate, sorbitol, sucralose, sucrose, tagatose, thaumatin, trehalose, xylitol or dextrin. In some aspects, the sugar is dextrin. Sugars are useful for restoring energy levels in the mammal body during and after food or alcohol poisoning.

Salts, minerals and sugar need to be replenished during and after food or alcohol poisoning or a training session. By combining these ingredients together with the probiotic *Pediococcus pentosaceus* and yeast, the composition of the invention can be used for treatment and/or prevention of food and alcohol poisoning or for treatment of muscle aches. Known compositions may include a probiotic or a mineral or minerals and vitamins. Some known composition may even include yeast and minerals. The composition of the invention comprises a unique combination of specific ingredients at specific ratios that allows for an improved recovery from food or alcohol poisoning, optionally together with antibiotics.

In some aspects, the composition comprises or consists of
0.1 to 5 or 10 wt %, at $10^3$ to $10^{11}$ CFU/g *Pediococcus pentosaceus*, and
1 to 50 wt % at $10^5$ to $10^{15}$ CFU/g one or more yeast, such as any brewer's yeast or *Saccharomyces cerevisiae* wherein a weight ratio of *Pediococcus pentosaceus*:yeast is between 0.01 to 0.5:1.

In some aspects, the composition comprises or consists of
0.1 to 5 or 10 wt %, at $10^3$ to $10^{11}$ CFU/g *Pediococcus pentosaceus*,
1 to 50 wt % at $10^5$ to $10^{15}$ CFU/g one or more yeast, such as any brewer's yeast or *Saccharomyces cerevisiae*, wherein a weight ratio of *Pediococcus pentosaceus*:yeast is between 0.01 to 0.5:1,
1 to 80 wt %, or 1 to 30 wt % one or more minerals, and optionally 1 to 40 wt % sugar, and up to 100 wt % pharmaceutical acceptable excipients, additives and/or adjuvants.

In some aspects, the composition comprises or consists of
0.1 to 5 or 10 wt %, at $10^3$ to $10^{11}$ CFU/g *Pediococcus pentosaceus*,
1 to 50 wt %, at $10^5$ to $10^{15}$ CFU/g one or more yeast, such as any brewer's yeast or *Saccharomyces cerevisiae*, wherein a weight ratio of *Pediococcus pentosaceus*:yeast is between 0.01 to 0.5:1,
1 to 80 wt %, or 1 to 30 wt % one or more minerals,
1 to 40 wt % sugar, and optionally up to 100 wt % pharmaceutical acceptable excipients, additives and/or adjuvants.

In some aspects, the composition comprises or consists of
0.1 to 2 wt %, at $10^5$ to $10^9$ CFU/g *Pediococcus pentosaceus*, and
1 to 25 wt % at $10^7$ to $10^{11}$ CFU/g one or more yeast, such as any brewer's yeast or *Saccharomyces cerevisiae*, wherein a weight ratio of *Pediococcus pentosaceus*:yeast is between 0.01 to 0.5:1.

In some aspects, the composition comprises or consists of
0.1 to 2 wt %, at $10^5$ to $10^9$ CFU/g *Pediococcus pentosaceus*,
1 to 25 wt % at $10^7$ to $10^{11}$ CFU/g one or more yeast, such as any brewer's yeast or *Saccharomyces cerevisiae*, wherein a weight ratio of *Pediococcus pentosaceus*:yeast is between 0.01 to 0.1:1,
1 to 75 wt % one or more minerals, and
optionally 1 to 30 wt % sugar, and up to 100 wt % pharmaceutical acceptable excipients, additives and/or adjuvants.

In some aspects, the composition comprises or consists of
0.1 to 1 wt %, at $10^6$ to $10^8$ CFU/g *Pediococcus pentosaceus*,
1 to 10 wt % at $10^8$ to $10^{10}$ CFU/g one or more yeast, such as any brewer's yeast or *Saccharomyces cerevisiae*, wherein a weight ratio of *Pediococcus pentosaceus*:yeast is between 0.01 to 0.1:1,
1 to 75 wt % one or more minerals, and optionally 1 to 25 wt % sugar, and up to 100 wt % pharmaceutical acceptable excipients, additives and/or adjuvants.

In some aspects, the composition comprises or consists of
0.1 to 1 wt %, at $10^6$ to $10^8$ CFU/g *Pediococcus pentosaceus*,
1 to 10 wt % at $10^8$ to $10^{10}$ CFU/g one or more yeast, such as any brewer's yeast or *Saccharomyces cerevisiae*, wherein a weight ratio of *Pediococcus pentosaceus*:yeast is between 0.01 to 0.1:1,
1 to 75 wt % one or more minerals, and
1 to 20 wt % sugar,
optionally up to 100 wt % pharmaceutical acceptable excipients, additives and/or adjuvants.

In some aspects, the composition comprises
0.1 to 1 wt %, or 0.1 to 0.6 wt %, at $0.5\times10^7$ to $9\times10^7$, or at $0.5\times10^7$ to $7\times10^7$ or at $0.5\times10^7$ to $5\times10^7$ or at $0.5\times10^7$ to $4\times10^7$ or at $1\times10^7$ to $3\times10^7$ CFU/g *Pediococcus pentosaceus*, and
0.1 to 8.5 wt %, or 1 to 7 wt %, at $1\times10^9$ to $4\times10^9$ CFU/g one or more yeast, such as *Saccharomyces cerevisiae*, wherein a weight ratio of *Pediococcus pentosaceus*:yeast is between 0.01 to 0.5:1

In some these aspects, the minerals are selected from the group comprising or consisting of zinc, magnesium, sodium and calcium. In some aspects, the minerals are selected from the group comprising or consisting of zinc sulfate, magnesium oxide, sodium chloride and calcium carbonate.

In some aspects, the composition comprises
0.1 to 1 wt %, or 0.1 to 0.6 wt %, at $0.5\times10^7$ to $9\times10^7$, or at $0.5\times10^7$ to $7\times10^7$ or at $0.5\times10^7$ to $5\times10^7$ or at $0.5\times10^7$ to $4\times10^7$ or at $1\times10^7$ to $3\times10^7$ CFU/g *Pediococcus pentosaceus*,
0.1 to 8.5 wt %, or 1 to 7 wt %, at $1\times10^9$ to $4\times10^9$ CFU/g one or more yeast, such as *Saccharomyces cerevisiae*, wherein a weight ratio of *Pediococcus pentosaceus*:yeast is between 0.01 to 0.1:1,
1 to 80 wt % one or more minerals, such as calcium phosphate, calcium chloride, calcium carbonate, calcium citrate and/or calcium ascorbate
optionally 1 to 20 wt % dextrin, and
optionally 0 to 75 wt % or up to 100 wt % pharmaceutical acceptable excipients, additives and/or adjuvants.

In some aspects, the excipients/additives/adjuvants is cellulose. In some aspects, the cellulose is selected from the group comprising or consisting of microcrystalline cellulose (E460i) and powdered cellulose (E460ii), hydroxyethyl cellulose, hydroxypropyl cellulose, hydroxyethyl methylcellulose, hydroxypropyl methylcellulose (HPMC), methylcellulose, ethylcellulose, ethyl methylcellulose, ethyl hydroxyethyl cellulose, carboxymethyl cellulose, or any combination thereof. In some aspects, the cellulose is microcrystalline cellulose.

In some aspects, the excipients/additives/adjuvants includes an anti-caking agent, such as magnesium salts of fatty acids, e.g. magnesium stearate. In some aspects, the excipients/additives/adjuvants include microcrystalline cellulose and magnesium stearate.

In some aspects, the one or more yeast is a bakery or brewer's yeast or any *Saccharomyces cerevisiae* strain from the *Saccharomyces* Genome Database (SGD).

In some aspects, the one or more yeast is a *Saccharomyces cerevisiae* strain selected from the group comprising or consisting of *S. cerevisiae* strain Kyokai no. 7 (K7), *S. cerevisiae* strain ATCC 204508, *S. cerevisiae* strain S288c, *S. cerevisiae* strain YGL118W, *S. cerevisiae* strain YBR134C, *S. cerevisiae* strain YDL102W, *Saccharomyces cerevisiae* var. *boulardii*, *Saccharomyces cerevisiae* var. *boulardii* Hansen CBS 5926, *S. cerevisiae* strain CNCM I-1079, *S. cerevisiae* strain DBVPG6763, or mixtures thereof. In some aspects, the one or more yeast is *Saccharomyces cerevisiae* var. *boulardii*. Several different stains of *Saccharomyces cerevisiae* var. *boulardii* have been tested. The same results have been obtained using different strains. Some *Saccharomyces cerevisiae* var. *boulardii* strains seem to work better than the other, at least when it comes to preventing and treating alcohol poisoning. However, they all reduce the effect of alcohol poisoning when present in the composition of the invention. In some aspects, the yeast is *Saccharomyces cerevisiae* var. *boulardii* strain CNCM I-1079 or strain DBVPG6763.

In some aspects, *Pediococcus pentosaceus* is selected from the group comprising or consisting of *P. pentosaceus* CRAG3, *P. pentosaceus* SP2, *P. pentosaceus* OA1 and *P. pentosaceus* S3N3, *P. pentosaceus* SWU73571, *P. pentosaceus* DSM 16,244, *P. pentosaceus* Q6, *P. pentosaceus* 4012, *P. pentosaceus* SL001, *P. pentosaceus* PP8, *P. pentosaceus* B49, *P. pentosaceus* S22, *P. pentosaceus* ICVB491, *P. pentosaceus* ICVB491, *P. pentosaceus* LUHS183, *pentosaceus* UR1, *P. pentosaceus* T1, *P. pentosaceus* UR1 [, *P. pentosaceus* Z13P, *P. pentosaceus* BaltBio02, *P. pentosaceus* SK25, *P. pentosaceus* 411, *P. pentosaceus* MP12, *P. pentosaceus* TG2, *P. pentosaceus* No. 183, *P. pentosaceus* KCC-23, *P. pentosaceus* PPCS, *P. pentosaceus* HM, *P. pentosaceus* L006, *P. pentosaceus* K 23-2, *P. pentosaceus* LMQS 331.3, *P. pentosaceus* CFF4, *P. pentosaceus* (TC48), *P. pentosaceus* ST65ACC, *P. pentosaceus* UR1, *P. pentosaceus* DT016, *P. pentosaceus* ATCC 43,200, *P. pentosaceus* B49, *P. pentosaceus* GS4, *P. pentosaceus* AK-23, *P. pentosaceus* ON89A, *pentosaceus* KFT18, *P. pentosaceus* NB-17, *P. pentosaceus* Sn26, *P. pentosaceus* M41, *P. pentosaceus* SL4, *P. pentosaceus* CRAG3, *P. pentosaceus* FP3, *P. pentosaceus* S-SU6, *P. pentosaceus* MYU 759, *P. pentosaceus* AR243, *P. pentosaceus* DK1, *P. pentosaceus* LAB6, *P. pentosaceus* LP28, *P. pentosaceus* KID7, *P. pentosaceus* FB145, *P. pentosaceus* FB181, *P. pentosaceus* xy46, *P. pentosaceus* CFR R38 and R35, *P. pentosaceus* CFR R123, *P. pentosaceus* GY23, *P. pentosaceus* HN8, *P. pentosaceus* SB83, *P. pentosaceus* ATCC 43,200 and *P. pentosaceus* KID7, *P. pentosaceus* GS4, *P. pentosaceus* MZF16, *P. pentosaceus* HUG0702, *P. pentosaceus* LI05, *P. pentosaceus* CRAG3 and *P. pentosaceus* HH-PP57, or mixtures thereof. Several different stains of *P. pentosaceus P. pentosaceus* have been tested. The same results have been obtained using different strains. Some *P. pentosaceus* strains seem to work better than the other, at least when it comes to preventing and treating alcohol poisoning. However, they all reduce the effect of alcohol poisoning. In some aspects, *Pediococcus pentosaceus* is *P. pentosaceus* HH-PP57.

In some aspects, *Pediococcus pentosaceus* is *P. pentosaceus* HH-PP57, the yeast is *Saccharomyces cerevisiae* var. *boulardii*, strain CNCM I-1079 or strain DBVPG6763 and the one or more minerals are selected from the group comprising or consisting of zinc, magnesium, calcium and sodium. In some aspects, *Pediococcus pentosaceus* is *P. pentosaceus* HH-PP57, the yeast is *Saccharomyces cerevisiae* var. *boulardii*, strain CNCM I-1079 or strain DBVPG6763 and the one or more minerals are selected from the group comprising or consisting of zinc sulfate, magnesium oxide, calcium carbonate and sodium chloride and the sugar is dextrin.

Some aspects relate to a dosage form comprising the composition as defined anywhere herein in the form of one solid dosage form, e.g. a capsule. Some aspects relate to a dosage form comprising the composition as defined anywhere herein in the form of two capsule. The composition may thus be divided over two capsules or tablets or sachets, each comprising or consisting of half the composition of the invention as defined anywhere herein.

The invention also relates to the composition as defined anywhere herein, for use in treatment and/or prevention of a disease in a mammal, such as a human.

The invention also relates to a composition comprising or consisting of *Pediococcus pentosaceus*, one or more yeast, one or more minerals, and optionally sugar, and pharmaceutical acceptable excipients, additives and/or adjuvants, for use in treatment and/or prevention of a disease in a mammal, such as a human.

In some aspects, the composition comprises or consists of *Pediococcus pentosaceus* in an amount of 10 wt % or less, or 5 wt % or less at $10^3$ to $10^{15}$ CFU/g, one or more yeast in an amount of 50 wt % or less at $10^5$ to $10^{15}$ CFU/g, wherein a weight ratio of *Pediococcus pentosaceus*:yeast is between 0.01 to 0.5:1, and/or zinc salt or zinc sulfate in an amount of 0.01 to 5 wt %, and/or sodium salt or sodium chloride in an amount of 0.01 to 90 wt %, and/or magnesium salt or magnesium oxide in an amount of 0.01 to 20 wt % and/or calcium salt or calcium carbonate in an amount of 0.01 to 50 wt %, wherein weight percentages are percentages of the total composition, and optionally 1 to 40 wt % sugar, and up to 100 wt % pharmaceutical acceptable excipients, additives and/or adjuvants, for use in treatment and/or prevention of a disease in a mammal, such as a human.

The invention also relates to the composition as defined anywhere herein, for use in treatment and/or prevention of food poisoning. The invention also relates to the composition as defined anywhere herein, for use in treatment and/or prevention of alcohol poisoning. The invention also relates to the composition as defined anywhere herein, for use in increasing a metabolism of alcohol in the human body by at least 20%, or 30%, or 40% or 50%, or 60%, or 70%, or 80%.

The composition of the invention is believed to improve the recovery from alcohol poisoning with at least 50%, i.e. the time needed to recover from alcohol poisoning or a "hangover" may be reduced by 50%. Hangovers are mainly caused by metabolic products of alcohol, such as acetaldehyde, present in the human body. Preferably, the composition of the invention increases the removal of the metabolic products of alcohol from the human body. The composition of the invention may therefore have socioeconomical advantages, when less resources are needed to overcome food and alcohol poisoning, such as reduced hospital visits, reduced absence from work, etc.

The invention also relates to the composition as defined anywhere herein, for use in treatment and/or prevention of (acute) diarrhoea or fatigue.

The invention also relates to the composition as defined anywhere herein, for use in treatment and/or prevention of oral rehydration therapy or muscle aching.

The invention also relates to the composition as defined anywhere herein, for use in treatment and/or prevention of antibiotic-associated diarrhea.

The invention also relates to a food supplements comprising or consisting of the composition as defined anywhere herein.

BRIEF DESCRIPTION OF THE DRAWINGS

The invention will now be explained more closely by the description of different embodiments of the invention and with reference to the appended FIGURES.

DETAILED DESCRIPTION OF VARIOUS EMBODIMENTS OF THE INVENTION

Definitions

As used herein "dextrins" means a group of low-molecular-weight carbohydrates produced by the hydrolysis of starch or glycogen. Dextrins are mixtures of polymers of D-glucose units linked by α- or α-glycosidic bonds. CAS number 337376-15-5.

As used herein "*Pediococcus pentosaceus*" means any strain of the *P pentosaceus* known to be useful as a probiotic.

As used herein "yeast" means any nutritional yeast, such as bakery/brewery yeast, such as *Saccharomyces* strains having probiotic activity. Yeast is not a bacteria.

As used herein "minerals" includes minerals, metals and salts oxides or sulfates or carbonates thereof.

As used herein the expression "one or more" means that the there may be one of the feature or more than one.

As used herein "composition" may be one or two dosage forms (e.g. one or two tablet or one or two capsule), which together comprise or consist of the ingredients described in this description.

As used herein the expression "hangover" means alcohol poisoning.

Composition

The invention relates to a composition for use in treatment of diseases or for use as a food supplement. The composition comprises or consists of *Pediococcus pentosaceus*, one or more yeast, and optionally one or more minerals, sugar and pharmaceutical acceptable excipients, additives and/or adjuvants.

*P. pentosaceus* may be present in an amount of 10 wt % or less at $10^3$ to $10^{15}$ CFU/g and the one or more yeast may be present in an amount of 50 wt % or less at $10^5$ to $10^{15}$ CFU/g, wherein weight percentages are percentages of the total composition. *P. pentosaceus* may be present in an amount of 5 wt % or less at $10^3$ to $10^{15}$ CFU/g and the one or more yeast may be present in an amount of 30 wt % or less at $10^3$ to $10^{15}$ CFU/g. *P. pentosaceus* may be present in an amount of 0.5 wt % or less at $10^3$ to $10^{15}$ CFU/g and the one or more yeast may be present in an amount of 20 wt % or less at $10^5$ to $10^{15}$ CFU/g. *P. pentosaceus* may be present in an amount of 5 wt % or less at $10^5$ to $10^8$ CFU/g and the one or more yeast may be present in an amount of 10 wt % or less at $10^5$ to $10^{15}$ CFU/g. *P. pentosaceus* may be present in an amount of 1 wt % or less at $10^5$ to $10^8$ CFU/g and the one or more yeast may be present in an amount of 10 wt % or less at $10^5$ to $10^{15}$ CFU/g. *P. pentosaceus* may be present in an amount of 0.5 wt % or less at $10^5$ to $10^8$ CFU/g and the one or more yeast may be present in an amount of 10 wt % or less at $10^5$ to $10^{15}$ CFU/g. The CFU of *P. pentosaceus* may be $10^6$ to $10^8$ CFU/g, or $10^7$ to $10^8$ CFU/g in combination with any of the weight percentages mentioned herein. The CFU of yeast may be $10^6$ to $10^{12}$ CFU/g, or $10^7$ to $10^{11}$ CFU/g in combination with any of the weight percentages mentioned herein.

The weight ratio of *Pediococcus pentosaceus*:yeast in the composition of the invention may be between 0.001 to 0.6:1. The ratio may be between 0.01 to 0.15:1, or 0.03 to 0.09:1.

The one or more yeast may be selected from the group comprising *S. cerevisiae* strain Kyokai no. 7 (K7), *S. cerevisiae* strain ATCC 204508, *S. cerevisiae* strain S288c, *S. cerevisiae* strain YGL118W, *S. cerevisiae* strain YBR134C, *S. cerevisiae* strain YDL102W, *Saccharomyces cerevisiae* var. *boulardii* and *Saccharomyces cerevisiae* var. *boulardii* Hansen CBS 5926, or mixtures thereof. The one or more yeast may be *Saccharomyces cerevisiae* var. *boulardii*. The one or more yeast may be *Saccharomyces cerevisiae* var. *boulardii*. CNCM I-1079. The one or more yeast may be *Saccharomyces cerevisiae* var. *boulardii*. strain DBVPG6763. *Pediococcus pentosaceus* may be selected from the group comprising *P. pentosaceus* CRAG3, *P. pentosaceus* SP2, *P. pentosaceus* OA1 and *P. pentosaceus* S3N3, *P. pentosaceus* SWU73571, *P. pentosaceus* DSM 16,244, *P. pentosaceus* Q6, *P. pentosaceus* 4012, *P. pentosaceus* SL001, *P. pentosaceus* PP8, *P. pentosaceus* B49, *P. pentosaceus* S22, *P. pentosaceus* ICVB491, *P. pentosaceus* ICVB491, *P. pentosaceus* LUHS183, *pentosaceus* UR1, *P. pentosaceus* T1, *P. pentosaceus* UR1 [, *P. pentosaceus* Z13P, *P. pentosaceus* BaltBio02, *P. pentosaceus* SK25, *P. pentosaceus* 411, *P. pentosaceus* MP12, *P. pentosaceus* TG2, *P. pentosaceus* No. 183, *P. pentosaceus* KCC-23, *P. pentosaceus* PPCS, *P. pentosaceus* HM, *P. pentosaceus* L006, *P. pentosaceus* K 23-2, *P. pentosaceus* LMQS 331.3, *P. pentosaceus* CFF4, *P. pentosaceus* (TC48), *P. pentosaceus* ST65ACC, *P. pentosaceus* UR1, *P. pentosaceus* DT016, *P. pentosaceus* ATCC 43,200, *P. pentosaceus* B49, *P. pentosaceus* GS4, *P pentosaceus* AK-23, *P. pentosaceus* ON89A, *pentosaceus* KFT18, *P. pentosaceus* NB-17, *P. pentosaceus* Sn26, *P. pentosaceus* M41, *P. pentosaceus* SL4, *P. pentosaceus* CRAG3, *P. pentosaceus* FP3, *P. pentosaceus* S-SU6, *P. pentosaceus* MYU 759, *P. pentosaceus* AR243, *P. pentosaceus* DK1, *P. pentosaceus* LAB6, *P. pentosaceus* LP28, *P. pentosaceus* KID7, *P. pentosaceus* FB145, *P. pentosaceus* FB181, *P. pentosaceus* xy46, *P. pentosaceus* CFR R38 and R35, *P. pentosaceus* CFR R123, *P. pentosaceus* GY23, *P. pentosaceus* HN8, *P. pentosaceus* SB83, *P. pentosaceus* ATCC 43,200 and *P. pentosaceus* KID7, *P. pentosaceus* GS4, *P. pentosaceus* MZF16, *P. pentosaceus* HLJG0702, *P. pentosaceus* LI05, *P. pentosaceus* CRAG3 and P. *Pentosaceus* HH-PP57, or mixtures thereof. *Pediococcus pentosaceus* may be *P. pentosaceus* strain HH-PP57.

The composition may comprise or consist of *Pediococcus pentosaceus*, one or more yeast, one or more minerals, and optionally sugar, and pharmaceutical acceptable excipients, additives and/or adjuvants.

The mineral may be zinc salt or zinc sulfate. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g and zinc salt or zinc sulfate may be present in an amount of 0.01 to 4.5 wt %, wherein weight percentages are percentages of the total composition. Or, *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g and zinc salt or zinc sulfate may be present in an amount of 0.01 to 4 wt %. Or, *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g and zinc salt or zinc sulfate may be present in an amount of 0.01 to 3 wt %. *P. pentosaceus* may be present in an amount of 0.5 wt % or less at $10^3$ to $10^{15}$ CFU/g, the one or more yeast may be present in an amount of 10 wt % or less at $10^5$ to $10^{15}$ CFU/g and zinc salt or zinc sulfate may be present in an amount of 0.01 to 2 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g and zinc salt or zinc sulfate may be present in an amount of 0.01 to 1 wt %. *P. pentosaceus* may be present in an amount of 0.5 or 1 wt % or less at $10^5$ to $10^8$ CFU/g, the one or more yeast may be present in an amount of 10 wt % or less at $10^5$ to $10^{15}$ CFU/g and zinc salt or zinc sulfate may be present in an amount of 0.1 to 1 wt %. The CFU of *P. pentosaceus* may be $10^6$ to $10^8$ CFU/g, or $10^7$ to $10^8$ CFU/g in combination with any of the weight percentages mentioned herein. The CFU of yeast may be $10^6$ to $10^{12}$ CFU/g, or $10^7$ to $10^{11}$ CFU/g in combination with any of the weight percentages mentioned herein.

The mineral may be magnesium salt or magnesium oxide. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g and magnesium salt or magnesium oxide may be present in an amount of 0.01 to 20 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g and magnesium salt or magnesium oxide may be present in an amount of 0.01 to 15 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g and magnesium salt or magnesium oxide may be present in an amount of 0.1 to 15 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g and magnesium salt or magnesium oxide may be present in an amount of 0.1 to 12 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g and magnesium salt or magnesium oxide may be present in an amount of 0.5 to 10 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g and magnesium salt or magnesium oxide may be present in an amount of 1 to 10 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g and magnesium salt or magnesium oxide may be present in an amount of 1 to 10 wt %. The CFU of *P. pentosaceus* may be $10^6$ to $10^8$ CFU/g, or $10^7$ to $10^8$ CFU/g in combination with any of the weight percentages mentioned herein. The CFU of yeast may be $10^6$ to $10^{12}$ CFU/g, or $10^7$ to $10^{11}$ CFU/g in combination with any of the weight percentages mentioned herein.

The mineral may be magnesium salt or magnesium oxide and zinc salt or zinc sulfate. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g, zinc salt or zinc sulfate may be present in an amount of 0.01 to 5 wt %, and magnesium salt or magnesium oxide may be present in an amount of 0.01 to 17 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g, zinc salt or zinc sulfate may be present in an amount of 0.01 to 4 wt % and magnesium salt or magnesium oxide may be present in an amount of 0.01 to 15 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g, zinc salt or zinc sulfate may be present in an amount of 0.01 to 3 wt % and magnesium salt or magnesium oxide may be present in an amount of 0.1 to 15 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 2 wt % and magnesium salt or magnesium oxide may be present in an amount of 0.1 to 12 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 1 wt % and magnesium salt or magnesium oxide may be present in an amount of 0.5 to 10 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt % and magnesium salt or magnesium oxide may be present in an amount of 1 to 10 wt %. %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt % and magnesium salt or magnesium oxide may be present in an amount of 1 to 10 wt %. The CFU of *P. pentosaceus* may be $10^6$ to $10^8$ CFU/g, or $10^7$ to $10^8$ CFU/g in combination with any of the weight percentages mentioned herein. The CFU of yeast may be $10^6$ to $10^{12}$ CFU/g, or $10^7$ to $10^{11}$ CFU/g in combination with any of the weight percentages mentioned herein.

The mineral may be calcium salt or calcium carbonate. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g and calcium salt or calcium carbonate may be present in an amount of 0.01 to 45 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g and calcium salt or calcium carbonate may be present in an amount of 0.1 to 40 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g and calcium salt or calcium carbonate may be present in an amount of 1 to 30 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g and calcium salt or calcium carbonate may be present in an amount of 5 to 30 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g and calcium salt or calcium carbonate may be present in an amount of 5 to 25 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g and calcium salt or calcium carbonate may be present in an amount of 5 to 20 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g and calcium salt or calcium carbonate may be present in an amount of 5 to 20 wt %. The CFU of *P. pentosaceus* may be $10^6$ to $10^8$ CFU/g, or $10^7$ to $10^8$ CFU/g in combination with any of the weight percentages mentioned herein. In some aspects, the CFU of yeast may be $10^6$ to $10^{12}$ CFU/g, or $10^7$ to $10^{11}$ CFU/g in combination with any of the weight percentages mentioned herein.

The mineral may be calcium salt or calcium carbonate and zinc salt or zinc sulfate. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g, zinc salt or zinc sulfate may be present in an amount of 0.01 to 5 wt % and calcium salt or calcium carbonate may be present in an amount of 0.01 to 45 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g, zinc salt or zinc sulfate may be present in an amount of 0.01 to 4 wt % and calcium salt or calcium carbonate may be present in an amount of 0.1 to 40 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g, zinc salt or zinc sulfate may be present in an amount of 0.01 to 3 wt % and calcium salt or calcium carbonate may be present in an amount of 1 to 30 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 2 wt % and calcium salt or calcium carbonate may be present in an amount of 5 to 30 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 1 wt % and calcium salt or calcium carbonate may be present in an amount of 5 to 25 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt % and calcium salt or calcium carbonate may be present in an amount of 5 to 20 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt % and calcium salt or calcium carbonate may be present in an amount of 5 to 20 wt %. The CFU of *P. pentosaceus* may be $10^6$ to $10^8$ CFU/g, or $10^7$ to $10^8$ CFU/g in combination with any of the weight percentages mentioned herein. In some aspects, the CFU of yeast may be $10^6$ to $10^{12}$ CFU/g, or $10^7$ to $10^{11}$ CFU/g in combination with any of the weight percentages mentioned herein.

The mineral may be calcium salt or calcium carbonate, magnesium salt or magnesium oxide and zinc salt or zinc sulfate. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g, zinc salt or zinc sulfate may be present in an amount of 0.01 to 5 wt %, magnesium salt or magnesium oxide may be present in an amount of 0.01 to 20 wt % and calcium salt or calcium carbonate may be present in an amount of 0.01 to 50 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g, zinc salt or zinc sulfate may be present in an amount of 0.01 to 4 wt %, magnesium salt or magnesium oxide may be present in an amount of 0.01 to 15 wt % and calcium salt or calcium carbonate may be present in an amount of 0.1 to 40 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g, zinc salt or zinc sulfate may be present in an amount of 0.01 to 3 wt %, magnesium salt or magnesium oxide may be present in an amount of 0.1 to 15 wt % and calcium salt or calcium carbonate may be present in an amount of 1 to 30 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 2 wt %, magnesium salt or magnesium oxide may be present in an amount of 0.1 to 12 wt % and calcium salt or calcium carbonate may be present in an amount of 5 to 30 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 1 wt %, magnesium salt or magnesium oxide may be present in an amount of 0.5 to 10 wt % and calcium salt or calcium carbonate may be present in an amount of 5 to 25 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt %, magnesium salt or magnesium oxide may be present in an amount of 1 to 10 wt % and calcium salt or calcium carbonate may be present in an amount of 5 to 20 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt %, magnesium salt or magnesium oxide may be present in an amount of 1 to 10 wt % and calcium salt or calcium carbonate may be present in an amount of 5 to 20 wt %. The CFU of *P. pentosaceus* may be $10^6$ to $10^8$ CFU/g, or $10^7$ to $10^8$ CFU/g in combination with any of the weight percentages mentioned herein. In some aspects, the CFU of yeast may be $10^6$ to $10^{12}$ CFU/g, or $10^7$ to $10^{11}$ CFU/g in combination with any of the weight percentages mentioned herein.

The mineral may be sodium salt or sodium chloride. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g and sodium salt or sodium chloride may be present in an amount of 0.01 to 85 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g and sodium salt or sodium chloride may be present in an amount of 0.1 to 80 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g and sodium salt or sodium chloride may be present in an amount of 10 to 75 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g and sodium salt or sodium chloride may be present in an amount of 15 to 70 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g and sodium salt or sodium chloride may be present in an amount of 25 to 65 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g and sodium salt or sodium chloride may be present in an amount of 25 to 60 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g and sodium salt or sodium chloride may be present in an amount of 25 to 60 wt %. The CFU of *P. pentosaceus* may be $10^6$ to $10^8$ CFU/g, or $10^7$ to $10^8$ CFU/g in combination with any of the weight percentages mentioned herein. The CFU of yeast may be $10^6$ to $10^{12}$ CFU/g, or $10^7$ to $10^{11}$ CFU/g in combination with any of the weight percentages mentioned herein.

The mineral may be sodium salt or sodium chloride and zinc salt or zinc sulfate. In the composition, *P. pentosaceus*, which may be strain HH-PP57, may be present in an amount of wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g, zinc salt or zinc sulfate may be present in an amount of 0.01 to 5 wt % and sodium salt or sodium chloride may be present in an amount of 0.01 to 85 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g, zinc salt or zinc sulfate may be present in an amount of 0.01 to 4 wt % and sodium salt or sodium chloride may be present in an amount of 0.1 to 80 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g, zinc salt or zinc sulfate may be present in an amount of 0.01 to 3 wt % and sodium salt or sodium chloride may be present in an amount of 10 to 75 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 2 wt % and sodium salt or sodium chloride may be present in an amount of 15 to 70 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 1 wt % and sodium salt or sodium chloride may be present in an amount of 25 to 65 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt % and sodium salt or sodium chloride may be present in an amount of 25 to 60 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt % and sodium salt or sodium chloride may be present in an amount of 25 to 60 wt %. The CFU of *P. pentosaceus* may be $10^6$ to $10^8$ CFU/g, or $10^7$ to $10^8$ CFU/g in combination with any of the weight percentages mentioned herein. In some aspects, the CFU of yeast may be $10^6$ to $10^{12}$ CFU/g, or $10^7$ to $10^{11}$ CFU/g in combination with any of the weight percentages mentioned herein.

The yeast may be *Saccharomyces cerevisiae* var. *boulardii*, such as strain CNCM I-1079 or strain DBVPG6763. *Pediococcus pentosaceus* may be *P. pentosaceus* strain HH-PP57.

The mineral may be sodium salt or sodium chloride, zinc salt or zinc sulfate, and magnesium salt or magnesium oxide and/or calcium salt or calcium carbonate. In the composition, *P. pentosaceus*, which may be strain HH-PP57, may be present in an amount of 10 wt % or less at $10^3$ to $10^{15}$ CFU/g, the one or more yeast, which may be strain CNCM I-1079 or strain DBVPG6763, may be present in an amount of 50 wt % or less at $10^5$ to $10^{15}$ CFU/g, zinc salt or zinc sulfate may be present in an amount of 0.01 to 5 wt %, sodium salt or sodium chloride may be present in an amount of 0.01 to 85 wt %, and magnesium salt or magnesium oxide may be present in an amount of 0.01 to 20 wt % and/or calcium salt or calcium carbonate may be present in an amount of 0.01 to 50 wt %, wherein weight percentages are percentages of the total composition. *P. pentosaceus* may be present in an amount of 5 wt % or less at $10^3$ to $10^{15}$ CFU/g, the one or more yeast may be present in an amount of 30 wt % or less at $10^5$ to $10^{15}$ CFU/g, zinc salt or zinc sulfate may be present in an amount of 0.01 to 4 wt %, sodium salt or sodium chloride may be present in an amount of 0.1 to 80 wt %, and magnesium salt or magnesium oxide may be present in an amount of 0.01 to 15 wt % and/or calcium salt or calcium carbonate may be present in an amount of 0.1 to 40 wt %. *P. pentosaceus* may be present in an amount of 1 wt % or less at $10^3$ to $10^{15}$ CFU/g, the one or more yeast may be present in an amount of 20 wt % or less at $10^5$ to $10^{15}$ CFU/g, zinc salt or zinc sulfate may be present in an amount of 0.01 to 3 wt %, sodium salt or sodium chloride may be present in an amount of 10 to 75 wt %, and magnesium salt or magnesium oxide may be present in an amount of 0.1 to 15 wt % and/or calcium salt or calcium carbonate may be present in an amount of 1 to 30 wt %. *P. pentosaceus* may be present in an amount of 10 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 2 wt %, sodium salt or sodium chloride may be present in an amount of 15 to 70 wt %, and magnesium salt or magnesium oxide may be present in an amount of 0.1 to 12 wt % and/or calcium salt or calcium carbonate may be present in an amount of 5 to 30 wt %. *P. pentosaceus* may be present in an amount of 5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.01 to 1 wt %, sodium salt or sodium chloride may be present in an amount of 25 to 65 wt %, and magnesium salt or magnesium oxide may be present in an amount of 0.5 to 10 wt % and/or calcium salt or calcium carbonate may be present in an amount of 5 to 25 wt %. *P. pentosaceus* may be present in an amount of 1 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt %, sodium salt or sodium chloride may be present in an amount of 25 to 60 wt %, and magnesium salt or magnesium oxide may be present in an amount of 1 to 10 wt % and/or calcium salt or calcium carbonate may be present in an amount of 5 to 20 wt %. *P. pentosaceus* may be present in an amount of 0.5 wt % or less at $10^5$ to $10^8$ CFU/g, the one or more yeast may be present in an amount of 10 wt % or less at $10^5$ to $10^{15}$ CFU/g, zinc salt or zinc sulfate may be present in an amount of 0.1 to 1 wt %, sodium salt or sodium chloride may be present in an amount of 25 to 60 wt %, and magnesium salt or magnesium oxide may be present in an amount of 1 to 10 wt % and/or calcium salt or calcium carbonate may be present in an amount of 5 to 20 wt %. The CFU of *P. pentosaceus* may be $10^6$ to $10^8$ CFU/g, or $10^7$ to $10^8$ CFU/g in combination with any of the weight percentages mentioned herein. In some aspects, the CFU of yeast may be $10^6$ to $10^{12}$ CFU/g, or $10^7$ to $10^{11}$ CFU/g in combination with any of the weight percentages mentioned herein.

The composition may comprise and consist of
0.05 to 40 wt % or 20 wt % or 10 wt % or 5 wt % or less *P. pentosaceus* at $10^5$ to $10^8$ CFU/g, and
1 to 40 wt % or 20 wt % or 10 wt % or less of one or more yeast at $10^5$ to $10^{15}$ CFU/g, wherein a weight ratio of *Pediococcus pentosaceus*:yeast is between 0.01 to 0.5:1,
0 to 5 wt % or 2 wt %, or 1 wt % or 0.75 wt % or less of zinc salt or zinc sulfate,
0 to 20 wt % or 15 wt % or 10 wt % or 7.5 wt % or less of magnesium salt or magnesium oxide,
0 to 50 wt % or 40 wt % or 30 wt % or 20 wt % or less of calcium salt or calcium carbonate,
0 to 90 wt % or 80 wt % or 70 wt % or 50 wt % or less of sodium salt or sodium chloride,
0 to 50 wt % or 40 wt % or 30 wt % or 20 wt % or less of sugar or dextrin,
and optionally up to 100 wt % pharmaceutical acceptable excipients, additives and/or adjuvants, wherein weight percentages are percentages of the total composition.

Pharmaceutical acceptable excipients, additives and/or adjuvants refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio and/or that are approved or approvable by a regulatory agency or body, for example the Food and Drug Administration or the European Medicines Agency.

Conventional procedures for the selection and preparation of suitable pharmaceutical formulations are described in, for example, "Pharmaceuticals—The Science of Dosage Form Designs", M. E. Aulton, Churchill Livingstone, 1988.

For preparing the composition, inert, pharmaceutically acceptable carriers can be either solid or liquid. Solid form compositions include powders, tablets, dispersible granules, capsules, sachets, and suppositories. A solid carrier can be one or more substances, which may also act as diluents, flavoring agents, solubilizers, lubricants, suspending agents, binders, or tablet disintegrating agents; it can also be an encapsulating material.

Liquid form compositions include ointments, creams, gels, aqueous liquids, which may be suspensions or emulations (W/O or O/W).

If the composition is made into a tablet or capsule, the final tablet or capsule may have a weight of 250 to 2000 mg, or from 500 to 1500 mg, or from 500 to 1500 mg, or from 750 to 1250 mg or from 400 to 500 mg. The composition may be divided over two tablets or capsules or sachets and the like, each having a weight of 500 to 1000 mg.

The composition may be a liquid, such as a suspension or an O/W emulsion.

One or more pharmaceutical acceptable excipients, additives and/or adjuvants may be selected from the group comprising or consisting of cellulose, such as microcrystalline cellulose, potato fiber, rice fiber, psyllium, (poly)saccharide, glycol, propylene glycol, polyethylene glycol 400, monooleate, sorbitan monolaurate (Span 20), anionic or nonionic surfactants, anti-foaming agents, wetting agent, such as monopalmitate, sucrose dioleate, detergent, such as sorbitan monolaurate, triethanolamine oleate, PEG-8 laurate.solubilizer, such as monopalmitate (Tween 60), sodium oleate, polyoxyethylene stearate, magnesium stearate, potassium oleate, preservatives, such as sorbic acid, viscosity modifiers/suspending agents, such as cellulose derivatives (e.g., methylcellulose, microcrystalline cellulose, carboxymethylcellulose, ethylcellulose, hydroxyethylcellulose, hydroxypropyl cellulose and hydroxypropyl methylcellulose etc), clays (e.g., hectorite, bentonite, aluminium and/or magnesium silicate), natural gums (e.g., acacia, guar gum, tragacanth, xanthan gum, alginates, carrageenan and locust bean gum), synthetic polymers (e.g., carbomers, polyvinyl pyrrolidone, polyvinyl alcohol and poloxamer), and miscellaneous compounds (e.g., colloidal silicon dioxide and silicates).

The excipients/additives/adjuvants may be cellulose. The cellulose may be selected from the group comprising or consisting of microcrystalline cellulose (E460i) and powdered cellulose (E460ii), hydroxyethyl cellulose, hydroxypropyl cellulose, hydroxyethyl methylcellulose, hydroxypropyl methylcellulose (HPMC), methylcellulose, ethylcellulose, ethyl methylcellulose, ethyl hydroxyethyl cellulose, carboxymethyl cellulose, or any combination thereof. The cellulose may be hydroxypropyl methylcellulose.

Other additives may be synthetic polymers, such as polyvinylpyrrolidone (PVP) and polyethylene glycol (PEG), gelatin, sucrose, lactose, sorbitol, xylitol and mannitol. Further additives may be anti-caking agents such as magnesium stearate.

Any sugar commonly used in pharmaceutical compositions or food additives may be used. The sugar may be selected from the group comprising or consisting of fructose, sucrose, dextrose, acesulfame K, alitame, aspartame, dextrose, fructose, galactose, inulin, isomalt, lactitol, maltitol, maltose, mannitol, neohesperidin dihydrochalcone, saccharin, sodium cyclamate, sorbitol, sucralose, sucrose, tagatose, thaumatin, trehalose, xylitol or dextrin. The sugar may be dextrin.

The one or more minerals may be selected from the group comprising or consisting of calcium, sodium, zinc, potassium, magnesium, potassium chloride, sodium chloride, calcium phosphate, calcium chloride, calcium carbonate, calcium citrate and/or calcium ascorbate. The one or more minerals may be selected from the group comprising or consisting of zinc, magnesium, potassium chloride and sodium chloride. The one or more minerals may be selected from the group comprising or consisting of zinc, potassium chloride and sodium chloride. The one or more minerals may be selected from the group comprising or consisting of zinc, calcium, magnesium, potassium chloride and sodium chloride, or oxides or sulfates or carbonates thereof. The one or more minerals may be selected from the group comprising or consisting of zinc sulfate, magnesium oxide, potassium chloride and sodium chloride. The minerals may be selected from the group comprising or consisting of zinc, magnesium, sodium and calcium, or oxides or sulfates or carbonates thereof. The minerals may be selected from the group comprising or consisting of zinc sulfate, magnesium oxide, sodium chloride and calcium carbonate.

The composition can be manufactured in different ways. The composition may be manufactured in a process for preparation of a capsule/tablet comprising or consisting of the following steps.

a) Mixing *Pediococcus pentosaceus* together with yeast, minerals and a filler such as microcrystalline cellulose and stir for a period of time,
b) Adding further additives, such as sugar e.g. dextrin,
c) Adding water and granulating the mixture,
d) Drying the obtained granulate,
e) Milling the dried granulate,
f) Adding further additives, such as sodium stearyl fumarate,
g) Mixing the obtained mixture, and
h) Filling of the mixture in capsules or pressing the mixture into tablets.

The composition may be administered topically or orally. The composition may be administered orally. The composition may be administered intramusculary. The composition may be administered intravenously.

The optimum dosage and frequency of administration will depend on the particular condition being treated and its severity; the species; the age, sex, size and weight, diet, and general physical condition of the particular mammal; other medication the mammal may be taking; the route of administration; the formulation; and various other factors known to physicians and others skilled in the art. Administration may be done in one dosage form or two dosage forms. The two dosage form, which together comprise or contain the composition of the invention may be administered simultaneously.

The composition of the invention may be administered at the start of the first alcohol intake. Alcohol is expected to be removed from the body at an increased rate compared to when alcohol is administered without administration of the composition. The composition may be administered at the start of the alcohol intake and/or during and/or after alcohol intake. When the composition is administered during or (direct) after alcohol intake, the alcohol and its metabolic products are expected to be removed from the body at an increased rate compared to when alcohol is administered without administration of the composition.

In a dosage regime, the composition is administered at least together with the first alcohol consumption and together with the last alcohol consumption.

In an alternative dosage regime, the composition is administered at least together with the first alcohol consumption, two to three hours after the first alcohol consumption and together with the last alcohol consumption.

The composition of the present invention may be used in conjoint therapy with other conventional therapies used to linger symptoms accompanying food or alcohol poisoning.

One or more other conventional therapies may be selected from the group comprising analgesics/painkillers, antibiotics, bismuth subsalicylate (Ex. Pepto-Bismol), loperamide (Ex. Imodium), ginger root tea, green tea, and the like.

Medical Use

The composition of the invention may be used in treatment and/or prevention of a disease in a mammal, such as a human. The composition as defined anywhere herein, especially a composition comprising or consisting of *Pediococcus pentosaceus*, one or more yeast, and optionally one or more minerals, sugar and pharmaceutical acceptable excipients, additives and/or adjuvants, or a composition comprising or consisting of *Pediococcus pentosaceus*, one or more yeast, one or more minerals, and optionally sugar, pharmaceutical acceptable excipients, additives and/or adjuvants, may be used in treatment and/or prevention of food and/or alcohol poisoning. The one or more yeast may be *Saccharomyces cerevisiae* var. *boulardii*, such as strain CNCM I-1079 or strain DBVPG6763. The *Pediococcus pentosaceus* may be *P. pentosaceus* HH-PP57.

It is further believed that the composition as defined anywhere herein improves the recovery rate from obesity, Improves Irritable Bowel Syndrome, ameliorates progression of non-alcoholic fatty liver disease, alleviates ethanol-induced liver injury, inhibits bacterial and fungal growth, inhibits inflammatory effects, ameliorates cholesterol metabolism and some related diseases, promotes biotransformation and utilisation of nutrients, alleviates liver toxicity imposed by chronic heavy metal exposure (e.g. cadmium, lead).

It is yet further believed that the composition as defined anywhere herein reduces the length of acute diarrhoea duration in infant, children and adults with. It is yet further believed that the composition as defined anywhere herein improves mental health, life quality, fatigue, pain and/or inflammation markers for patients with MS, candidiasis, dyspledenia and small intestine bacterial overgrowth. The composition is believed to improve reestablishment of normal gut microbiota, reduce gut translocation of pathogen, proteolysis pathogenic toxins (*C. difficile, E. Coli*, Cholera, *H. pulori*), reduce mucositis, stimulate the immune system, reduce pro-inflammatory responses, promote mucosal anti-inflammatory signalling effects, reduce antibiotic associated diarrhoea, alleviate against traveller's diarrhoea.

The composition is believed to be useful in oral rehydration therapy and muscle aching. The composition is believed to counteract the side effects of antibiotics.

The composition as defined anywhere herein may be used for conjoint treatment. Such conjoint treatment may be achieved by way of the simultaneous, sequential or separate dosing of the individual compositions for the prevention and/or treatment defined herein.

The invention may relate to a pharmaceutical composition comprising (i) the composition as defined anywhere herein, and (ii) an additional pharmaceutical active ingredient, and optionally one or more pharmaceutically acceptable excipient, carrier or diluent.

The invention may relate to a pharmaceutical composition comprising (i) the composition as defined anywhere herein, and (ii) an additional pharmaceutical active ingredient, and (iii) one or more pharmaceutically acceptable excipient, carrier or diluent.

The additional pharmaceutical active ingredient may be an antibiotic, such as an antibiotic used for treatment of food poisoning. The additional pharmaceutical active ingredient may be a drug used for treatment of alcohol poisoning. The additional pharmaceutical active ingredient may be a drug used in treatment of overdosing of opiates and the like.

Examples of an additional pharmaceutical active ingredient may be bismuth subsalicylate (Pepto-Bismol) or loperamide (Imodium) acetaminophen (Tylenol) or ibuprofen (Advil).

Examples of an additional pharmaceutical active ingredient may be rifaximin (Xifaxan) link or rifamycin (Aemcolo), ciprofloxacin (Cipro), Levaquin, ondansetron (Zofran), azithromycin (Zithromax, Zmax) or amoxillin.

The composition as defined anywhere herein may be used as food supplement or together with other food supplements.

EXAMPLES

Example 1 of a 500 mg Dose

*Pediococcus pentosaceus, P. Pentosaceus* HH-PP57 at $3.0 \times 10^7$ cfu/g (Ca. 3 mg with Current Supplier)

Nutritional yeast, *Saccharomyces cerevisiae* var. *boulardii*: 200 mg
  Dextrin: 100 mg
  NaCl: 1.5 mg
  KCl: 10 mg
  Zink: 0.6 mg
  Microcrystalline cellulose and granulating agent: 184.9 mg

Example 2 of a 500 mg Dose

*Pediococcus pentosaceus, P. Pentosaceus* HH-PP57 at $1.5 \times 10^7$ cfu/Dose (Ca. 3 mg with Current Supplier)

Nutritional yeast, *Saccharomyces cerevisiae* var. *boulardii*: 200 mg
  Dextrin: 100 mg
  NaCl: 1.5 mg
  KCl: 10 mg
  Zink: 0.6 mg
  Microcrystalline cellulose and granulating agent: 184.9 mg.

Example 3

A tablet which also comprises magnesium and calcium.

| Ingredient | mg or cfu/g | /capsule | mg/capsule | wt % |
|---|---|---|---|---|
| P. Pentosaceus (cfu) HH-PP57 | $4.08 \times 10^7$ | $4.20 \times 10^7$ | 4.20 | 0.41 |
| S. Boulardii (cfu) CNCM I-1079 OR STRAIN DBVPG6763 | $1.46 \times 10^9$ | $1.50 \times 10^9$ | 68.18 | 6.63 |
| NaCl | 486.24 | 500 | 500.00 | 48.62 |
| ZnSO4 | 5.76 | 5.92 | 5.92 | 0.58 |
| Dextrin/Socker | 194.50 | 200 | 200.00 | 19.45 |
| MgO | 60.78 | 62.5 | 62.50 | 6.08 |
| CaCO3 | 182.34 | 187.5 | 187.50 | 18.23 |

Microcrystalline cellulose was used up to 100 wt %.

Example 4

The composition (1 tablet) of example 3 was tested on 11 healthy Caucasian volunteers, 8 male, 3 female.

| Example 4a Day 1 Time | 7 pm 1 tablet | Between 7-11:40 pm | | |
|---|---|---|---|---|
| Subject | Consumption | Consumption | Consumption | Consumption |
| 1 | Dinner | Red wine (2.5 dl) | whiskey (6 cl) | RB&vodka (4 cl) | GT (6 cl) |
| 2 | Dinner | White wine(2.5 dl) | whiskey (6 cl) | RB&vodka (4 cl) | GT (6 cl) |
| 3 | Dinner | Bier (4 dl) 5 vol % ethanol | whiskey (6 cl) | RB&vodka (4 cl) | GT (6 cl) |
| 4 | Dinner | Bier (4 dl) 5 vol % ethanol | whiskey (6 cl) | RB&vodka (4 cl) | GT (6 cl) |

| Example 4a Day 1-2 Time | 11:40 pm | Between 11:40 pm and 3 am | | |
|---|---|---|---|---|
| Subject | 1 tablet | Consumption | Consumption | Consumption | 3:00 am |
| 1 | RB&vodka (4 cl) | water (2 dl) | GT (4 cl) | water (2 dl) | water (2 dl) |
| 2 | RB&vodka (4 cl) | water (2 dl) | GT (4 cl) | GT (4 cl) | water (2 dl) |
| 3 | RB&vodka (4 cl) | water (2 dl) | GT (4 cl) | whiskey (6 cl) | water (2 dl) |
| 4 | RB&vodka (4 cl) | water (2 dl) | GT (4 cl) | Bier (4 dl) 5 vol % ethanol | water (2 dl) |

| Day 2 Time ethanol Subject | Result 9:00 am promillage | Consumption | 10:15 am promillage |
|---|---|---|---|
| 1 | 0 | | 0 |
| 2 | 0.32 | water (2 dl) + juice (2 dl) | 0 |
| 3 | 0.33 | water (2 dl) + juice (2 dl) | 0 |
| 4 | 0.34 | water (2 dl) + juice (2 dl) | 0.23 |

| Example 4b Day 1 Time | 7 pm 1 tablet | Between 9 and 11:40 pm | | |
|---|---|---|---|---|
| Subject | Consumption | Consumption | Consumption | Consumption |
| 1 | Dinner | Red wine (2.5 dl) | whiskey (6 cl) | RB&vodka (4 cl) | GT (6 cl) |
| 2 | Dinner | White wine (2.5 dl) | whiskey (6 cl) | RB&vodka (4 cl) | GT (6 cl) |
| 3 | Dinner | Bier (4 dl) 5 vol % ethanol | whiskey (6 cl) | RB&vodka (4 cl) | GT (6 cl) |
| 4 | Dinner | Bier (4 dl) 5 vol % ethanol | whiskey (6 cl) | RB&vodka (4 cl) | GT (6 cl) |

| Example 4b Day 1-2 | | Time | | | | |
|---|---|---|---|---|---|---|
| | 11:40 pm | Between 11:40 pm and 3 am | | | | |
| Subject | 1 tablet | Consumption | | Consumption | Consumption | 3:00 am |
| 1 | water (2 dl) | GT (4 cl) | water (2 dl) | RB&vodka (4 cl) | water (2 dl) | water (2 dl) |
| 2 | water (2 dl) | GT (4 cl) | water (2 dl) | RB&vodka (4 cl) | GT (4 cl) | water (2 dl) |
| 3 | water (2 dl) | GT (4 cl) | water (2 dl) | RB&vodka (4 cl) | whiskey (6 cl) | water (2 dl) |
| 4 | water (2 dl) | GT (4 cl) | water (2 dl) | RB&vodka (4 cl) | Bier (4 dl) 5 vol % ethanol | water (2 dl) |

| Day 2 Time ethanol Subject | Result 9:00 am promillage | Consumption | 10:15 am promillage |
|---|---|---|---|
| 1 | 0 | | 0 |
| 2 | 0.35 | water (2 dl) + juice (2 dl) | 0.12 |
| 3 | 0.35 | water (2 dl) + juice (2 dl) | 0 |
| 4 | 0.32 | water (2 dl) + juice (2 dl) | 0.18 |

| Example 4c Day 1 Time | 8 pm 1 tablet | Between 8 and 10:30 pm | 10:30 pm 1 tablet |
|---|---|---|---|
| Subject | | Consumption | Consumption |
| 5 | Dinner | Bier (7.5 dl) 11.5 vol % ethanol | Bier (7.5 dl) 6.2 vol % ethanol |

| Example 4c Day 2 Time Subject | 1:30 am Consumption | 2:00 am Consumption | 2:44 am Consumption | Expected promille 1.47 |
|---|---|---|---|---|
| 5 | whiskey (5 cl) | whiskey (5 cl) | whiskey (5 cl) | |

| Day 2 Time ethanol Subject | Result 9.12 am promillage | Expected promille |
|---|---|---|
| 5 | 0.18 | 0.58 |

| | | | Time | | | |
|---|---|---|---|---|---|---|
| Example 4d Day 1 | 6 pm 1 tablet | 6:30 pm Consumption | 7:30 pm Consumption | | 9:00 pm 9:30 pm Consumption | |
| 5 | Red wine (2.5 dl) | Pisco sour (5 cl), 40 vol % ethanol | Dinner | Red wine (2.5 dl) | water (2 dl) | Bier (33 dl) 6.5 vol % ethanol |
| 6 | Red wine (2.5 dl) | Pisco sour (5 cl), 40 vol % ethanol | Dinner | Red wine (2.5 dl) | water (2 dl) | Bier (33 dl) 6.5 vol % ethanol |
| 7 | Red wine (2.5 dl) | Pisco sour (5 cl), 40 vol % ethanol | Dinner | Red wine (2.5 dl) | water (2 dl) | Red wine (2.5 dl) |
| 8 | Red wine (2.5 dl) | Pisco sour (5 cl), 40 vol % ethanol | Dinner | Red wine (2.5 dl) | water (2 dl) | Bier (33 dl) 6.5 vol % ethanol |
| 9 | Red wine (2.5 dl) | Pisco sour (5 cl), 40 vol % ethanol | Dinner | Red wine (2.5 dl) | water (2 dl) | Red wine (2.5 dl) |
| 10 | Red wine (2.5 dl) | Pisco sour (5 cl), 40 vol % ethanol | Dinner | Red wine (2.5 dl) | water (2 dl) | Bier (33 dl) 6.5 vol % ethanol |
| 11 | Red wine (2.5 dl) | Pisco sour (5 cl), 40 vol % ethanol | Dinner | Red wine (2.5 dl) | water (2 dl) | Red wine (2.5 dl) |

| | | | Time | | | |
|---|---|---|---|---|---|---|
| Example 4d Day 2 | 9:30 pm | 10:00 pm Consumption | 11:00 pm Consumption | 12:00 pm | 1:00 am Consumption | 2:00 am |
| 5 | water (2 dl) | GT (5 cl) | Red wine (2.5 dl) | water (2 dl) | Bier (33 dl) 6.5 vol % ethanol | water (2 dl) |
| 6 | water (2 dl) | Red wine (2.5 dl) | Red wine (2.5 dl) | water (2 dl) | Bier (33 dl) 6.5 vol % ethanol | water (2 dl) |
| 7 | water (2 dl) | Bier (33 dl) 6.5 vol % ethanol | Red wine (2.5 dl) | water (2 dl) | Bier (33 dl) 6.5 vol % ethanol | water (2 dl) |
| 8 | water (2 dl) | Bier (33 dl) 6.5 vol % ethanol | Red wine (2.5 dl) | water (2 dl) | Bier (33 dl) 6.5 vol % ethanol | water (2 dl) |
| 9 | water (2 dl) | Red wine (2.5 dl) | Red wine (2.5 dl) | water (2 dl) | Red wine (2.5 dl) | water (2 dl) |
| 10 | water (2 dl) | White wine (2.5 dl) | White wine (2.5 dl) | water (2 dl) | Bier (33 dl) 6.5 vol % ethanol | water (2 dl) |
| 11 | water (2 dl) | Red wine (2.5 dl) | Red wine (2.5 dl) | water (2 dl) | Red wine (2.5 dl) | water (2 dl) |

| Day 2 Time ethanol Subject | Result 9.25 am promillage |
|---|---|
| 5 | 0.1 |
| 6 | 0.18 |
| 7 | 0.26 |
| 8 | 0.08 |
| 9 | 0.33 |
| 10 | 0 |
| 11 | 0.3 |

GT=gin (xcl) with tonic water up to 3 dl, RB&vodka=vodka (xcl) with red bull up to 3 dl Consumption=ethanol consumption Subjects 6, 7 and 9 were females, all others were male, all ages between 18 and 50 years old.

Figure 1:
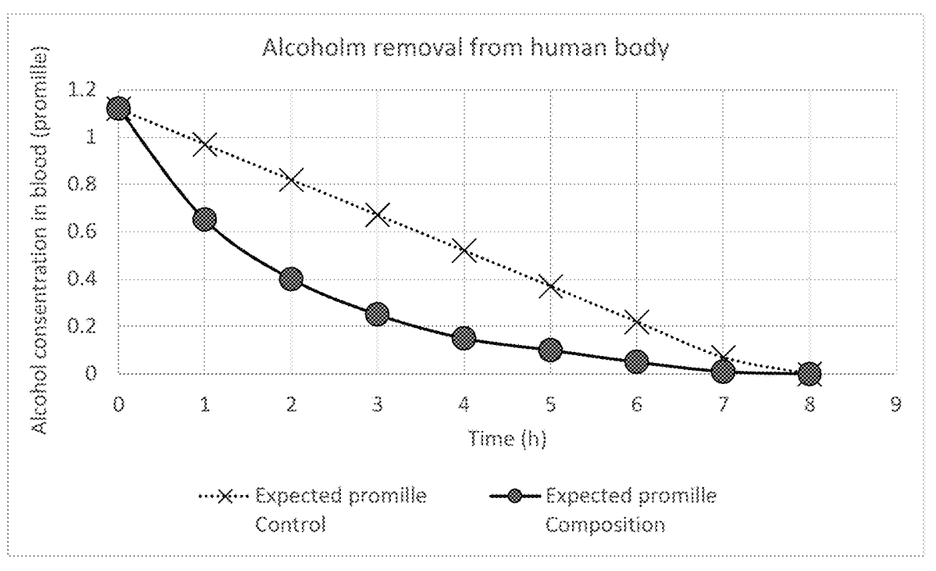
FIG. 1 shows a graph visualizing reduction of alcohol from the human body with and without administration of the composition of the invention at the start of the alcohol intake at time o hours.

As predicted in FIG. 1, the results in example 4 clearly show an increase in removal of alcohol from the human body, or increased metabolism of ethanol in the human body. All subjects drank excessive amounts of alcohol over a period of 6 to 8 hours. 6 to 7 hours after stopping the alcohol intake, almost all volunteers showed a minimum alcohol level using the breathing test that would allow them to drive a car in some countries.

Because the composition increases removal of alcohol in the body it is believed to be useful in treatment of alcohol poisoning.

Example 5

Two capsules were made comprising together the following ingredients

| Ingredient | cfu/capsule | mg/capsule | wt % |
|---|---|---|---|
| P. Pentosaceus (cfu) HH-PP57 | $1.10 \times 10^7$ | 2.10 | 0.41 |
| S. Boulardii (cfu) CNCM I-1079 OR STRAIN DBVPG6763 | $0.75 \times 10^9$ | 34.09 | 6.63 |
| NaCl | | 250.00 | 48.62 |
| ZnSO4 | | 2.96 | 0.58 |
| Dextrin/Socker | | 0 | 0 |
| MgO | | 30.75 | 6.08 |
| CaCO3 | | 93.50 | 18.23 |
| Microcrystalline callulose | | | Up to 100 |

Magnesium stearate was used in amounts of less than 0.5 wt % or 0.05 wt %. Microcrystalline cellulose was used up to 100 wt %.

Examples 6, Study Protocol

| Example 6 Day 1 Time Subject | 5 pm 2 capsules Consumption | | 6 pm Consumption | 7 pm Consumption |
|---|---|---|---|---|
| 12 to 24 | Dinner/120 g hamburger with fries | vodka (6 cl) | vodka (6 cl) | vodka (6 cl) |

| Subject | Pediococcus Pentosaceus Strain | Result Day 1 '7:15 pm ethanol promillage | Consumption | Result Day 1, '9:15 am ethanol promillage |
|---|---|---|---|---|
| 12 | GY23 (Creative enzymes, USA) | 0.65-1.20 | water | 0.00-0.04 |
| 13 | HH-PP57 (Probioway Co., Ltd.) | 0.65-1.20 | water | 0.00-0.04 |
| 14 | g-SL-1 (Creative Biolabs, USA) | 0.65-1.20 | water | 0.00-0.04 |
| 15 | JMC 5885 (ATCC) | 0.65-1.20 | water | 0.00-0.04 |
| 16 | DSM 20333 (ATCC) | 0.65-1.20 | water | 0.00-0.04 |
| 17 | NCDO 1859 (ATCC) | 0.65-1.20 | water | 0.00-0.04 |
| 18 | NCDO 990 (ATCC) | 0.65-1.20 | water | 0.00-0.04 |
| 19 | PN1011 (ATCC) | 0.65-1.20 | water | 0.00-0.04 |
| 20 | bMx# 0711603 (ATCC) | 0.65-1.20 | water | 0.00-0.04 |
| 21 | 32 (Creative Biolabs, USA) | 0.65-1.20 | water | 0.00-0.04 |
| 22 | Z2 (Creative Biolabs, USA) | 0.65-1.20 | water | 0.00-0.04 |
| 23 | 529 (Creative Biolabs, USA) | 0.65-1.20 | water | 0.00-0.04 |
| 24 | 35694 (Creative Biolabs, USA) | 0.65-1.20 | water | 0.00-0.04 |

A control, not using the composition of the invention is estimated to have an alcohol metabolism at an average rate of 0.015 g/100 mL/hour, which is the same as reducing aBAC level (grams of alcohol in 100 milliliters of blood) by 0.015 per hour. The expected promille for such a control person at 7:15 pm would be about 1%.

The results are expected to show that the composition of the invention increases the removal of alcohol from the human body.

The results are also expected to show that different strains of *Pediococcus pentosaceus* can be used to obtain the same results.

The invention claimed is:

1. A composition comprising
   0.1 to 5 wt %, $10^3$ to $10^{11}$ CFU/g *Pediococcus Pentosaceus*, wherein *P. pentosaceus* is the sole bacterium in the composition,
   1 to 50 wt % at $10^5$ to $10^{15}$ CFU/g one or more yeast, which is any brewer's yeast or *Saccharomyces cerevisiae*, wherein the weight ratio of *Pediococcus Pentosaceus*:yeast is between 0.01 to 0.1:1,
   1 to 80 wt % one or more minerals, and one or more pharmaceutical acceptable excipients, additives and/or adjuvants, and
   optionally 1 to 40 wt % sugar,
   wherein the composition is in the form of a pharmaceutically acceptable tablet or capsule.

2. The composition according to claim 1, wherein the composition consists of:
   the *Pediococcus Pentosaceus*, the yeast, the one or more minerals and the one or more pharmaceutical acceptable excipients, additives and/or adjuvants.

3. The composition according to claim 1, wherein the composition comprises or consist of
   0.1 to 2 wt %, at $10^5$ to $10^9$ CFU/g of the *Pediococcus Pentosaceus*,
   1 to 25 wt % at $10^7$ to $10^{11}$ CFU/g of the one or more yeast, which is any brewer's yeast or *Saccharomyces*

*cerevisiae*, wherein the ratio weight ratio of *Pediococcus Pentosaceus*: yeast is between 0.01 to 0.1:1,
1 to 75 wt % of the one or more minerals, and
optionally 1 to 30 wt % of the sugar.

4. The composition according to claim 1, wherein the weight ratio of *Pediococcus Pentosaceus*: yeast is between 0.04 to 0.08:1.

5. The composition according to claim 1, wherein the amount of the *P. pentosaceus* is 1 wt % or less at $10^5$ to $10^8$ CFU/g.

6. The composition according to claim 1, wherein the one or more minerals are selected from the group consisting of zinc, magnesium, sodium and calcium.

7. The composition according to claim 1, wherein the one or more minerals comprise zinc salt or zinc sulfate in an amount of 0.01 to 5 wt %.

8. The composition according to claim 1, wherein the the one or more minerals comprise magnesium salt or magnesium oxide in an amount of 0.01 to 20 wt %.

9. The composition according to claim 1, wherein the the one or more minerals comprise calcium salt or calcium carbonate in an amount of 0.01 to 50 wt %.

10. The composition according to claim 1, wherein the the one or more minerals comprise sodium salt or sodium chloride in an amount of 0.01 to 90 wt %.

11. The composition according to claim 1, wherein the composition comprises
0.05-0.1 to 5 wt % of the *P. pentosaceus* at $10^5$ to $10^8$ CFU/g,
1 to 40 wt % of the one or more yeast at $10^5$ to $10^{15}$ CFU/g, wherein the weight ratio of *Pediococcus Pentosaceus*: yeast is between 0.01 to 0.1:1,
0 to 5 wt % of zinc salt or zinc sulfate,
0 to 20 wt % of magnesium salt or magnesium oxide,
0 to 50 wt % of calcium salt or calcium carbonate,
0 to 90 wt % of sodium salt or sodium chloride,
0 to 50 wt % of sugar or dextrin.

12. The composition according to claim 1, wherein the sugar is selected from the group consisting of fructose, sucrose, dextrose, acesulfame k, alitame, aspartame, dextrose, fructose, galactose, inulin, isomalt, lactitol, maltitol, maltose, mannitol, neohesperidin dihydrochalcone, saccharin, sodium cyclamate, sorbitol, sucralose, sucrose, tagatose, thaumatin, trehalose, xylitol and dextrin, or mixtures thereof.

13. The composition according to claim 1, wherein the excipients/additives/adjuvants are selected from the group consisting of cellulose, microcrystalline cellulose, potato fiber, rice fiber, psyllium, (poly)saccharides, glycol, propylene glycol, polyethylene glycol 400, monooleate, sorbitan monolaurate, anionic or nonionic surfactants, anti-foaming agents, wetting agents, monopalmitate, sucrose dioleate, detergents, sorbitan monolaurate, triethanolamine oleate, PEG-8 laurate, solubilizers, monopalmitate, sodium oleate, polyoxyethylene stearate, magnesium stearate, potassium oleate, preservatives, sorbic acid, viscosity modifiers/-suspending agents, methylcellulose, microcrystalline cellulose, carboxymethylcellulose, ethylcellulose, hydroxyethylcellulose, hydroxypropyl cellulose, hydroxypropyl methylcellulose, clays, hectorite, bentonite, aluminium and/or magnesium silicate, natural gums, acacia gum, guar gum, tragacanth, xanthan gum, alginates, carrageenan, locust bean gum, synthetic polymers, carbomers, polyvinyl pyrrolidone, polyvinyl alcohol and, poloxamer, colloidal silicon dioxide and silicates.

14. The composition according to claim 1, wherein the excipients/additives/adjuvants are microcrystalline cellulose and magnesium stearate.

15. The composition according to claim 1, wherein the composition comprises 0.1 to 5 wt % of the *P. pentosaceus* at $10^5$ to $10^8$ CFU/g, and
1 to 20 wt % of the one or more yeast at $10^5$ to $10^{15}$ CFU/g, wherein the weight ratio of *Pediococcus Pentosaceus*: yeast is between 0.01 to 0.1:1,
2 wt %, or less of zinc salt or zinc sulfate,
15 wt % or less of magnesium salt or magnesium oxide,
40 wt % or less of calcium salt or calcium carbonate,
80 wt % or less of sodium salt or sodium chloride, and
40 wt % or less of sugar or dextrin.

16. The composition according to claim 1, wherein the composition comprises
0.05-0.1 to 5 wt % of the *P. pentosaceus* at $10^5$ to $10^8$ CFU/g, and
1 to 10 wt % of the one or more yeast at $10^5$ to $10^{15}$ CFU/g, wherein the weight ratio of *Pediococcus Pentosaceus*: yeast is between 0.01 to 0.1:1,
0.75 wt % or less of zinc salt or zinc sulfate,
7.5 wt % or less of magnesium salt or magnesium oxide,
20 wt % or less of calcium salt or calcium carbonate,
50 wt % or less of sodium salt or sodium chloride,
20 wt % or less of sugar or dextrin.

* * * * *